Oct. 30, 1956 A. P. HOWARD Plant Pat. 1,525
HYBRID TEA ROSE PLANT
Filed June 29, 1955
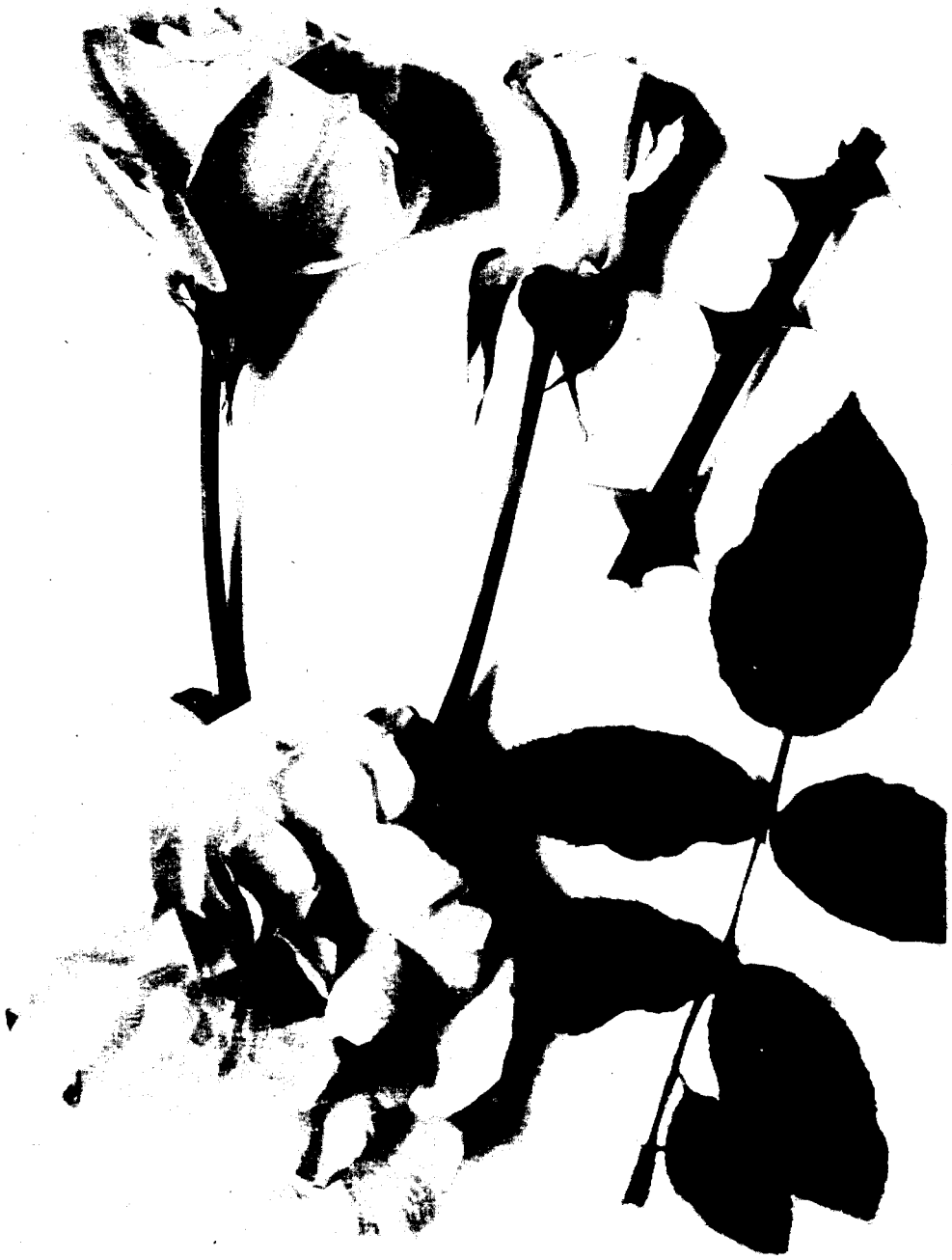
INVENTOR
Arthur Preston Howard
By Orville M. Kile
Plant Patent Agent United States Patent Office Plant Pat. 1,525

Patented Oct. 30, 1956

1,525

HYBRID TEA ROSE PLANT

Arthur Preston Howard, Sierra Madre, Calif., assignor to Howard & Smith, Montebello, Calif.

Application June 29, 1955, Serial No. 519,015

1 Claim. (Cl. 47—61)

My present invention relates to improvements in hybrid tea rose plants in the class producing yellow blooms. These improvements consist principally in vigorous growth, larger and stronger stems, and flowers which are more fragrant than any known yellow varieties, long-lasting, and retain their deep yellow color even in the hottest weather.

This new variety originated in our nurseries at Montebello, California, and resulted from a cross made by me between an unnamed seedling and the variety Ville de Paris (unpatented). It has been asexually reproduced by me at the same locality in southern California, by budding, and its outstanding characteristics appear to be firmly fixed.

Illustrations accompanying these specifications show three specimens of the bloom of my new variety in various stages of opening, together with a separate leaf and portion of stem—all in approximately their true colors.

In the following detailed description, color plate numbers indicate Ridgway's Color Standards and Nomenclature.

THE PLANT

Class: Hybrid tea.

Growth habit: Bushy and upright. Height 3 to 4 feet. Healthy and vigorous.

Blooming habit: Very floriferous throughout a nine months' blooming season in southern California climate.

Stems: Strong. Length about 2 feet. Color Olive Green (Plate IV) heavily overlaid with Maroon (Plate I).

*Thorns.*—Four to five between nodes. Point straight outward, reclining at point. ⅜ inch long. Color Ox-blood Red (Plate I).

Foliage:

*Type.*—Five to seven leaflets.

*Shape.*—Oval, with accuminate apex. Edge finely serrated.

*Size.*—Terminal leaflet averages 2 inches by 1¼ inches. Lateral leaflets considerably smaller.

*Texture.*—Coriaceous. Heavy in texture. Holds up well when cut.

*Quantity.*—Abundant.

*Color.*—Upper surface approximately Dark Cress Green (Plate XXXI). Under surface lighter.

*Stipules.*—Prominent. Points outward-curved.

*Rachis.*—Strong and smooth.

*Disease resistance.*—No diseases have been noted to date.

THE FLOWER

Bud:

*Size.*—Just before unfolding, approximately 1 inch wide by 1¾ inches long.

*Shape.*—Ovoid to blocky.

*Color.*—Light Cadmium (Plate IV).

*Sepals.*—Fairly simple. Reflex early. Approximately 1 inch by 1½ inches.

*Calyx.*—Broad. Smooth.

*Peduncle.*—Rigid. Usually overlaid with Maroon (Plate I). No thorns or prickles present.

Bloom:

*Borne.*—Singly, on long stems.

*Size.*—Medium, averaging 3½ inches across and with a depth of 1½ inches.

*Form.*—Rounded into deep cupshape, opening informally.

*Color.*—Lemon Chrome (Plate IV), retaining color during hottest weather.

*Petalage.*—17 to 20 petals, so arranged as to make the flower look full.

*Fragrance.*—Intensely fragrant with tea quality.

*Longevity.*—Very long-lasting.

Petals:

*Shape.*—Orbicular.

*Edge.*—Slightly undulated.

*Substance.*—Flaccid.

*Size.*—Average about 1½ by 1½ inches.

*Behavior.*—Persistent. Clinging.

Reproductive organs:

*Pistils.*—Three to four. ⅛ inch long. Color Nopal Red (Plate I). *Styles* Deep Chrome (Plate III) and about ⅛ inch long. *Stigmas* Deep Chrome.

*Stamens.*—Number 50 to 60, surrounding pistils. *Filaments* short and Deep Chrome. *Anthers* same color as filaments and about ¼ inch long.

*Pollen.*—Average in amount.

*Receptacle.*—Not prominent. Deep Chrome in color.

COMPARISONS

The known varieties most like my new variety are Eclipse (Plant Patent No.162) and Mrs. E. P. Thom (unpatented). Principal differences are as follows:

*Compared with Eclipse*

1. The foliage of my variety is an improvement, being healthier, heavier in texture, wilts less quickly when cut, and is less prone to mildew.
2. The flower of my variety is much more fragrant, it being one of the most intensely fragrant yellow roses known.
3. The color of the bud and flower of my variety is deeper yellow.
4. The flower of my variety is much longer-lasting.
5. Shape of the bud of my variety is quite different, it being less slender and pointed than that of Eclipse.
6. Sepals of my variety are shorter, wider and less foliaceous.
7. Petals of my flower have different shape, being approximately round and slightly undulate on the edges.
8. The flowers of my variety hold their color in the hottest weather much better than do those of Eclipse.

*Comparison with Mrs. E. P. Thom*

1. The foliage of my variety is more desirable because of its abundance, health, darker green color, and heavier texture.
2. The bush of my new variety is more vigorous.
3. The flower stems of my new variety are longer and stronger.
4. The flower of my new variety is more intensely fragrant.
5. The flower of my variety holds its color much better in hottest weather.
6. The flowers of my variety are much larger.
7. The flowers of my variety are a deeper yellow color than the canary yellow of Mrs. E. P. Thom.

Having thus disclosed my invention, I claim:

The new and distinct variety of hybrid tea rose plant, substantially as herein shown and described, characterized particularly as to novelty by its vigorous healthy growth; its dark-green, abundant foliage; and its long-lasting, intensely fragrant flowers of deep yellow, which color is retained even during the hottest weather.

No references cited.